US00PP30058P2

(12) United States Plant Patent
Larsen

(10) Patent No.: US PP30,058 P2
(45) Date of Patent: Jan. 8, 2019

(54) **SUPER-MINIATURE *ROSA* PLANT NAMED 'QIR 1631'**

(50) Latin Name: *Rosa hybrida*
Varietal Denomination: QIR 1631

(71) Applicant: Michael Larsen, Sabro (DK)

(72) Inventor: Michael Larsen, Sabro (DK)

(73) Assignee: Q-Genetics ApS, Sabro (DK)

( * ) Notice: Subject to any disclaimer, the term of this patent is extended or adjusted under 35 U.S.C. 154(b) by 0 days.

(21) Appl. No.: 15/731,447

(22) Filed: Jun. 12, 2017

(51) Int. Cl.
*A01H 5/02* (2018.01)

(52) U.S. Cl.
USPC ..... Plt./129

(58) Field of Classification Search
USPC ..... Plt./101, 116, 129
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of Rose plant named 'QIR 1631', characterized by its upright and mounding plant habit; strong lateral branches; dark green-colored leaflets; large bright red purple-colored flowers; flowers held upright on strong and erect peduncles; and good postproduction longevity.

3 Drawing Sheets

Botanical designation: *Rosa hybrida.*
Cultivar denomination: 'QIR 1631'.

BACKGROUND OF THE INVENTION

The present Invention relates to a new and distinct cultivar of Rose or *Rosa* plant, botanically known as *Rosa hybrida*, commercially used as a potted Rose plant and hereinafter referred to by the name 'QIR 1631'.

The new Rose plant is a product of a planned breeding program conducted by the Inventor in Odense, Denmark. The objective of the breeding program was to develop new uniform and healthy potted Rose varieties with attractive flower colors and excellent postproduction longevity.

The new Rose plant originated from an open-pollination in April, 2012 of a proprietary selection of *Rosa hybrida* identified as code number 68, not patented, as the female, or seed, parent with a unknown proprietary selection of *Rosa hybrida* as the male, or pollen, parent. The new Rose plant was discovered and selected by the Inventor in May, 2013 as a single flowering plant within the progeny of the stated cross-pollination in a controlled greenhouse environment in Odense, Denmark.

Asexual reproduction of the new Rose plant by cuttings in a controlled greenhouse environment in Odense, Denmark since June, 2013 has shown that the unique features of this new Rose plant are stable and reproduced true to type in successive generations of asexual reproduction.

SUMMARY OF THE INVENTION

The following traits have been repeatedly observed and are determined to be the unique characteristics of 'QIR 1631'. These characteristics in combination distinguish 'QIR 1631' as a new and distinct Rose plant:

1. Upright and mounding plant habit.
2. Strong lateral branches.
3. Dark green-colored leaflets.
4. Large bright red purple-colored flowers.

5. Flowers held upright on strong and erect peduncles.
6. Good postproduction longevity.

Plants of the new Rose differ from plants of the female parent selection primarily in plant habit as plants of the new Rose are more compact and denser than plants of the female parent selection. In addition, flowers of plants of the new Rose are more intense red purple in color than flowers of plants of the female parent selection.

Plants of the new Rose can be compared to plants of the Rose 'QIR 1611', disclosed in a U.S. Plant patent application Ser. No. 15/731,444 filed concurrently. In side-by-side comparisons, plants of the new Rose differ primarily from plants of 'QIR 1611' in flower color as plants of 'QIR 1611' have bright red-colored flowers.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph on the first sheet comprises a side perspective view of a typical plant of 'QIR 1631' grown in a container.

The photograph on the second sheet is a close-up view of a typical open flower of 'QIR 1631'.

The photograph at the top of the third sheet is a close-up view of the upper and lower surfaces of typical flowers of 'QIR 1631'.

The photograph at the bottom of the third sheet is a close-up view of the upper and lower surfaces of typical leaves of 'QIR 1631'.

DETAILED BOTANICAL DESCRIPTION

Plants of the new Rose have not been observed under all possible combinations of environmental conditions and cultural practices. The phenotype may vary somewhat with variations in environmental conditions such as temperature and light intensity, without, however, any variance in genotype. The aforementioned photographs, following observations and measurements describe plants grown during the autumn in a glass-covered greenhouse in Odense, Denmark and under cultural practices typical of commercial potted Rose production. Plants were grown in 13-cm containers, pinched one time and were three months old when the photographs and description were taken. During the production of the plants, day and night temperatures averaged 21° C. and light levels ranged from 60 to 100 klux. In the following description, color references are made to The Royal Horticultural Society Colour Chart, 2001 Edition, except where general terms of ordinary dictionary significance are used.

Botanical classification: *Rosa hybrida* 'QIR 1631'.

Parentage:

*Female, or seed, parent*.—Proprietary selection of *Rosa hybrida* identified as code number 68, not patented.

*Male, or pollen, parent*.—Unknown proprietary selection of *Rosa hybrida*, not patented.

Propagation:

*Type*.—By cuttings.

*Time to produce a rooted young plant, summer*.—About 24 days at soil temperatures about 23° C.

*Time to produce a rooted young plant, winter*.—About 24 days at soil temperatures about 21° C.

*Root description*.—Fibrous, fine; close to 158B in color.

*Rooting habit*.—Freely branching; medium density.

Plant description:

*Plant and growth habit*.—Upright and mounding plant habit; moderately vigorous growth habit; freely branching habit, pinching enhances lateral branch development; dense and bushy appearance.

*Plant height*.—About 25 cm to 30 cm.

*Plant width* (*spread*).—About 20 cm to 25 cm.

*Lateral branches*.—Length: About 12 cm to 18 cm. Diameter: About 3 mm to 5 mm. Internode length: About 1 cm to 1.5 cm. Strength: Strong. Texture: Smooth, glabrous. Color: Close to 137A. Thorns: Density: About two to four per linear centimeter. Shape: Acicular with subulate apices. Height: About 3 mm to 5 mm. Diameter, at base: About 2 mm to 3 mm. Color, immature: Close to 199C. Color, mature: Close to 156A.

Leaf description:

*Arrangement*.—Alternate; compound with five leaflets per leaf.

*Leaf length*.—About 6 cm to 8 cm.

*Leaf width*.—About 4 cm to 6 cm.

*Terminal leaflet length*.—About 3 cm to 4 cm.

*Terminal leaflet width*.—About 2 cm to 3 cm.

*Lateral leaflet length*.—About 2 cm to 3 cm.

*Lateral leaflet width*.—About 1.5 cm to 2.5 cm.

*Leaflet shape*.—Ovate.

*Leaflet apex*.—Acuminate.

*Leaflet base*.—Obtuse.

*Leaflet margin*.—Serrate.

*Leaflet texture, upper and lower surfaces*.—Smooth, glabrous; somewhat leathery.

*Leaflet venation pattern*.—Pinnate; reticulate.

*Leaflet color*.—Developing leaflets, upper surface: Close to 136A. Developing leaflets, lower surface: Close to 191A and 174A. Fully developed, upper surface: Close to N189A; venation, close to 136A. Fully developed, lower surface: Close to 191A and 174A; venation, close to 137A.

*Petioles*.—Leaf petiole length: About 1 cm to 1.5 cm. Leaf petiole diameter: About 1 mm to 2 mm. Leaflet petiole length: Less than 1 mm to 1 mm. Leaflet petiole diameter: Less than 1 mm to 1 mm. Leaf petiole texture, upper surface: Minute pubescence. Leaf petiole texture, lower surface: Smooth, glabrous. Leaflet petiole texture, upper and lower surfaces: Smooth, glabrous. Leaf petiole color: Upper surface: Close to 137A. Lower surface: Close to 138B. Leaflet petiole color: Upper surface: Close to 137A. Lower surface: Close to 137B.

*Leaf stipules*.—Quantity: Two per leaf. Length: About 5 mm to 10 mm. Width: About 1 mm to 2 mm. Shape: Subulate. Apex: Acuminate. Base: Truncate; sessile. Margin: Dentate. Texture, upper and lower surfaces: Smooth, glabrous. Color, upper surface: Close to 137A. Color, lower surface: Close to 137C.

Flower description:

*Flower type and habit*.—Large double flowers with numerous petaloids; consistently symmetrical rosette flowers; flowers borne on strong and erect peduncles with one terminal flower per lateral branch; flowers face upright.

*Flowering season*.—Year-round under greenhouse conditions, optimal flowering from spring through autumn under garden conditions; plants begin flowering about five to seven weeks after planting.

*Post-production longevity*.—Good postproduction longevity, plants maintain good substance for about seven to nine weeks; flowers persistent.

*Fragrance*.—None detected.

*Flower diameter*.—About 5 cm to 6 cm.

*Flower depth* (*height*).—About 2 cm to 3 cm.

*Flower buds*.—Length: About 2 cm to 3 cm. Diameter: About 1 cm to 1.5 cm. Shape: Ovoid. Color: Close to 63A.

*Petals*.—Quantity: About four to five in a single whorl; petals imbricate. Length: About 3 cm to 3.5 cm. Width: About 3.5 cm to 4 cm. Shape: Obovate. Apex: Emarginate. Base: Attenuate. Margin: Entire. Texture, upper and lower surfaces: Smooth, glabrous; velvety. Color: When opening, upper surface: Close to N57A. When opening, lower surface: Close to 63A. Fully opened, upper surface: Close to N66A; color becoming closer to 61B with development. Fully opened, lower surface: Close to 61B.

*Petaloids*.—Quantity: About 30 to 50 arranged in numerous whorls; petaloids imbricate. Length: About 2.5 cm to 3.5 cm. Width: About 2.5 cm to 3 cm. Shape: Orbicular. Apex: Rounded. Base: Attenuate. Margin: Entire. Texture, upper and lower surfaces: Smooth, glabrous; velvety. Color: When opening, upper and lower surfaces: Close to N66A. Fully opened, upper and lower surfaces: Close to N66A.

*Sepals*.—Quantity and arrangement: Typically five in a single star-shaped whorl. Length: About 2.5 cm. Width: About 5 mm to 10 mm. Shape: Lanceolate. Apex: Acuminate. Base: Obtuse. Margin: Serrate; ciliate. Texture, upper and lower surfaces: Fine pubescence. Color: When opening, upper surface: Close to 144A. When opening, lower surface: Close to 138B. Fully opened, upper surface: Close to 138A. Fully opened, lower surface: Close to 138B.

*Peduncles*.—Length: About 2 cm to 3 cm. Diameter: About 2 mm. Strength: Strong. Aspect: Erect. Texture: Fine pubescence. Color: Close to 144A.

*Reproductive organs*.—Stamens: Quantity per flower: About 50 to 100. Anther length: About 2 mm to 3 mm. Anther shape: Elliptic. Anther color: Close to 16A. Filament color: Close to 157A. Pollen amount: Scarce. Pollen color: Close to 17B. Pistils: Quantity per flower: About 30 to 50. Pistil length: About 5 mm to 10 mm. Stigma shape: Round. Stigma color: Close to 161A. Style length: About 5 mm. Style color: Close to 53C. Receptacle height: About 1 cm. Receptacle diameter: About 5 mm to 10 mm. Receptacle shape: Cup-shaped. Receptacle texture: Smooth, glabrous. Receptacle color: Close to 137C. Fruits: Quantity per flower: One. Length: About 1 cm to 2 cm. Diameter: About 1.2 cm to 2.2 cm. Texture: Smooth, glabrous. Color: Close to 42B and 26A. Seeds: Quantity per fruit: About six to eight. Length: About 3 mm to 5 mm. Diameter: About 2 mm to 4 mm. Texture: Smooth, glabrous. Color: Close to 166B, 166C and 165C.

Pathogen & pest resistance: Plants of the new Rose have not been observed to be resistant to pathogens and pests common to Rose plants.

Temperature tolerance: Plants of the new Rose have been observed to tolerate temperatures ranging from about 3° C. to about 35° C. to 40° C.

It is claimed:

1. A new and distinct Super-miniature *Rosa* plant name 'QIR 1631' as illustrated and described.

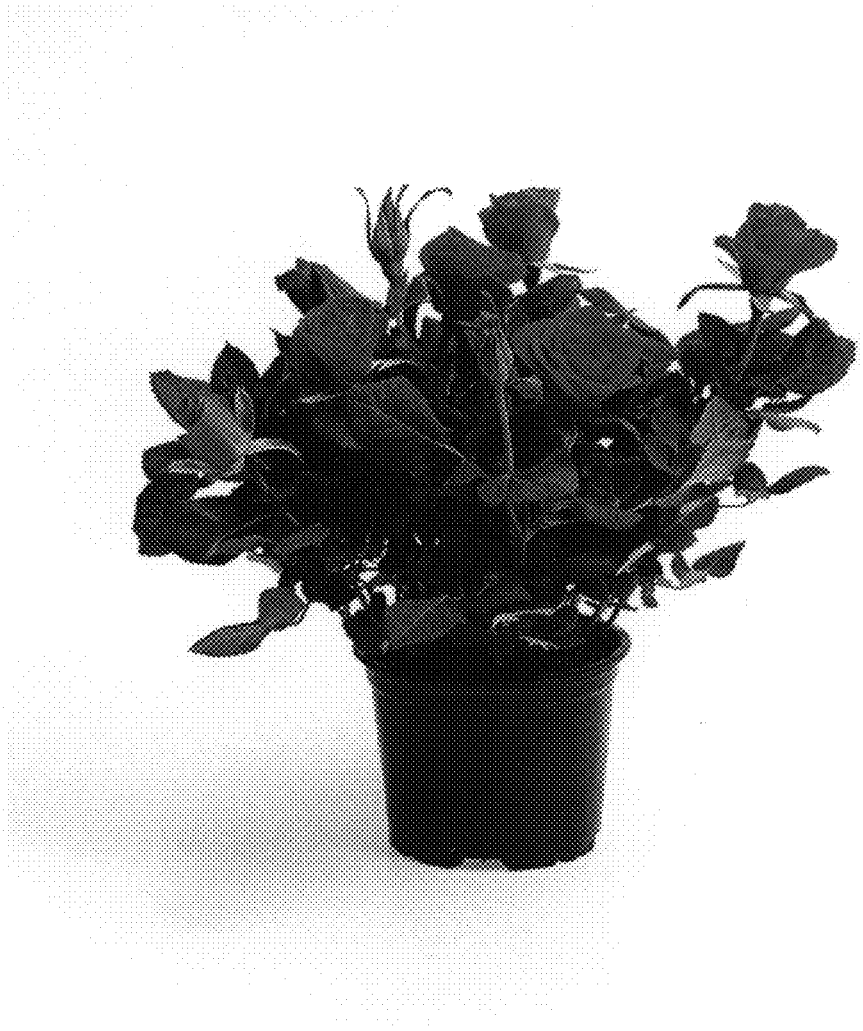

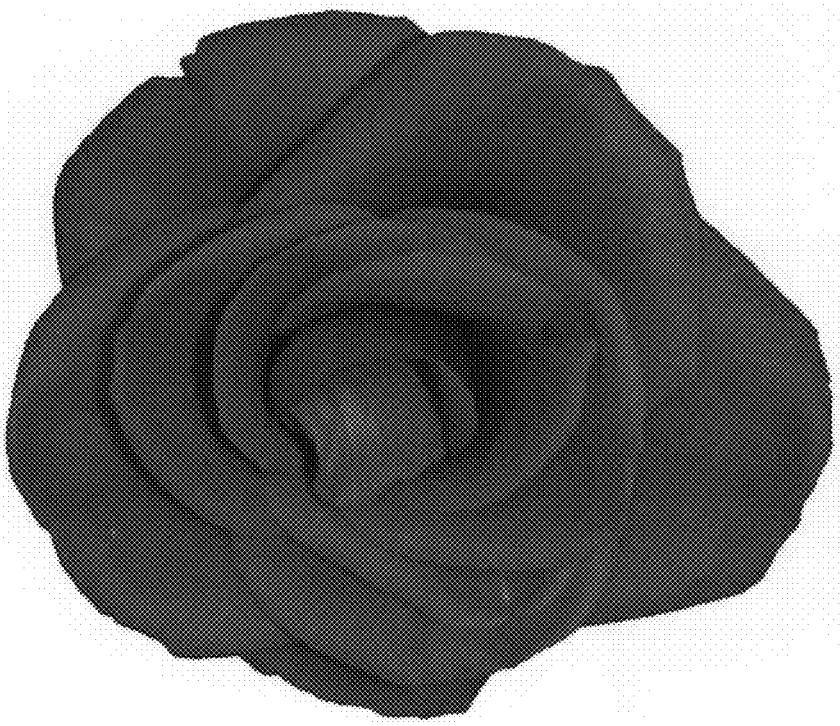

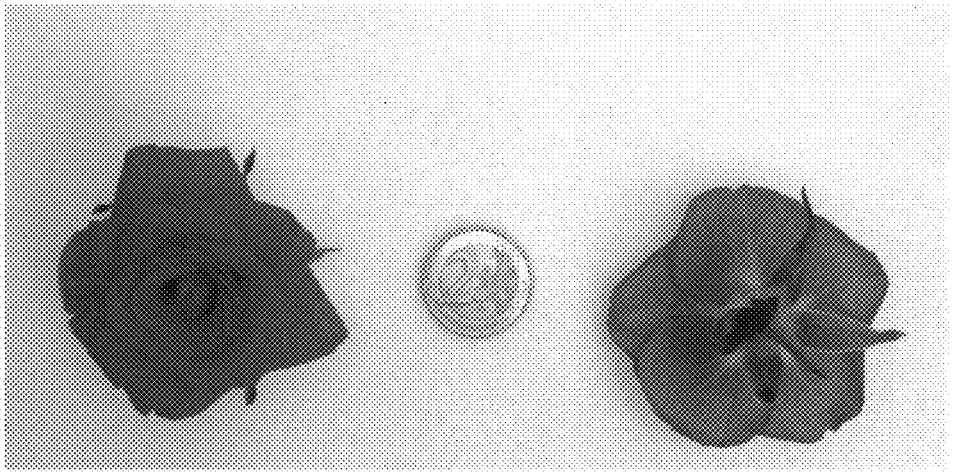
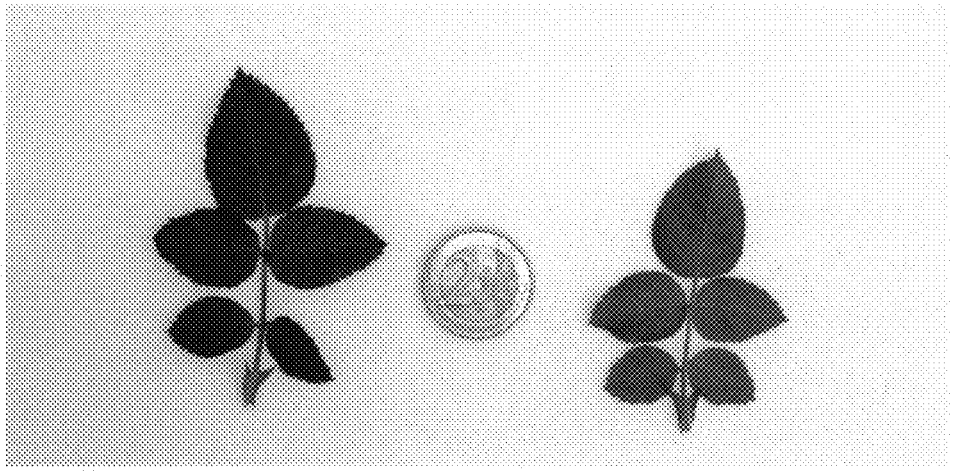

* * * * *